US00PP28477P2

(12) United States Plant Patent
Lief

(10) Patent No.: US PP28,477 P2
(45) Date of Patent: Oct. 3, 2017

(54) ***ANTHERICUM* PLANT NAMED 'STARLIGHT'**

(50) Latin Name: *Anthericum saundersiae*
Varietal Denomination: Starlight

(71) Applicant: Ian Desmond Lief, Durban (ZA)

(72) Inventor: Ian Desmond Lief, Durban (ZA)

( * ) Notice: Subject to any disclaimer, the term of this patent is extended or adjusted under 35 U.S.C. 154(b) by 17 days.

(21) Appl. No.: 14/998,800

(22) Filed: Feb. 17, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

A new cultivar of *Anthericum* 'Starlight' that is characterized by its variegated foliage with light yellow-green and creamy-white midribs, and multiple longitudinal stripes throughout the darker green leaf blade, its yellow-green inflorescence stalks and its ust growth habit, golden yellow colored flower buds, white flowers with yellow tips and bright yellow stamens, and its non-viable seeds.

2 Drawing Sheets

Botanical classification: *Anthericum saundersiae.*
Varietal denomination: 'Starlight'.

BACKGROUND OF THE INVENTION

The present invention relates to a new and distinct cultivar of *Anthericum saundersiae* and will be referred to hereafter by its cultivar name, 'Starlight'. The new cultivar of *Anthericum* lily grass is a new herbaceous perennial grown for container and landscape use.

The new cultivar, 'Starlight' arose as a naturally occurring shoot mutation on an unnamed and unpatented plant of *Anthericum saundersiae* in a garden in Durban, Kwazulu Natal, Republic of South Africa.

Asexual propagation of the new cultivar was first accomplished by shoot division in July of 2010 in Durban, Kwazulu Natal, Republic of South Africa. Asexual propagation by shoot division has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Starlight' as a distinct cultivar of *Anthericum.*

1. 'Starlight' exhibits variegated foliage with light yellow-green and creamy-white midribs, and multiple longitudinal stripes throughout the darker green leaf blade.
2. 'Starlight' exhibits light yellow-green inflorescence stalks.
3. 'Starlight' exhibits golden yellow colored flower buds.
4. 'Starlight' exhibits white flowers with yellow tips and bright yellow stamens.
5. 'Starlight' exhibits non-viable seeds that are sterile; germination produces white leaves that quickly die.

The parent plant of 'Starlight' differs from 'Starlight' in having green foliage and green flowering stalks. 'Starlight' can be most closely compared to the cultivars 'Agristripes' (not patented) and 'Variegata' (not patented). 'Agristripes' is similar to 'Starlight' in having variegated foliage and in having a compact plant habit. 'Agristripes' differs from 'Starlight' in having green inflorescence stalks, green flower stalks, dark green midribs, and in producing viable seeds. 'Variegata' differs from 'Starlight' in having flower stalks that are green in color, in having foliage variegation with green centers and white margins, and in producing viable seeds.

BRIEF DESCRIPTION OF THE DRAWINGS

The accompanying colored photographs illustrate the overall appearance and distinct characteristics of a 2 year-old plant of the new Anthericum as grown in a greenhouse in a 17-cm container in Boskoop, Netherlands.

The photograph in FIG. 1 provides a side view of 'Starlight' in bloom.

Figure 1:
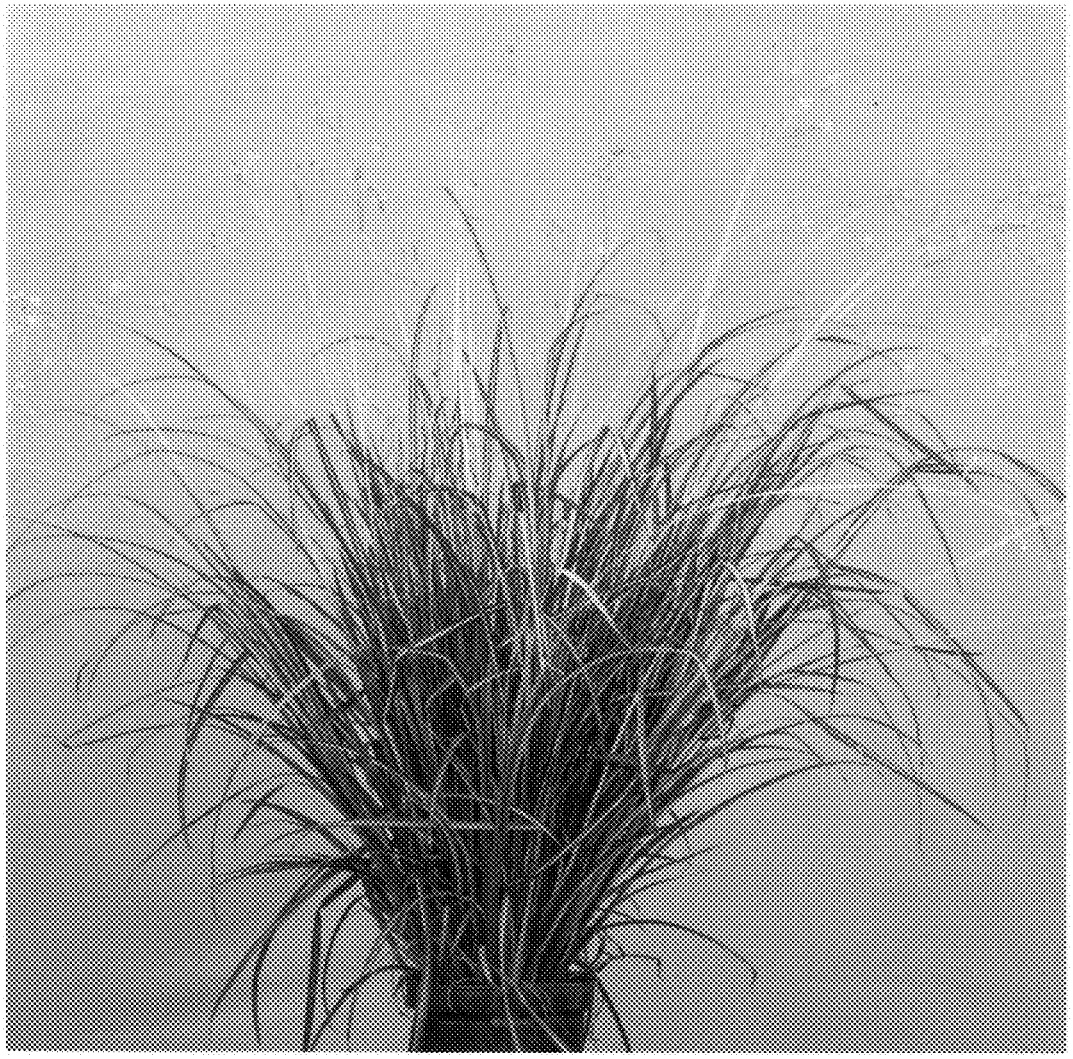
Figure 2:
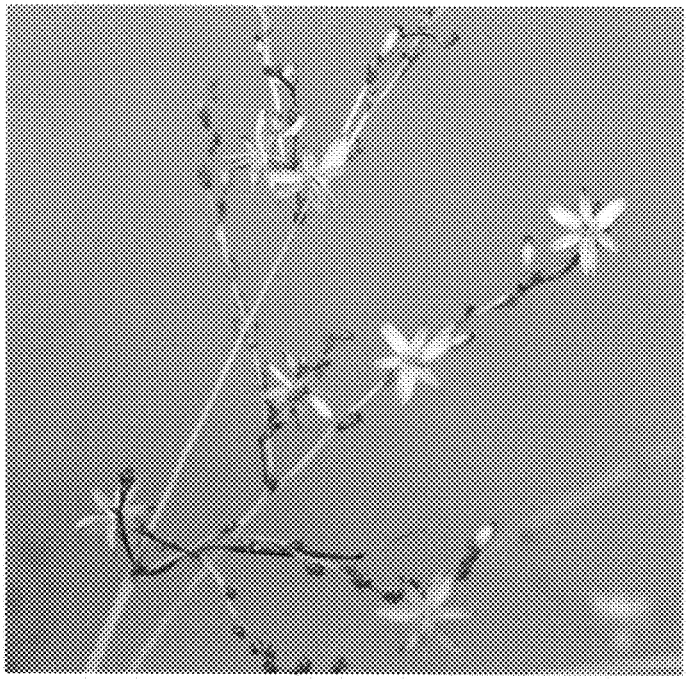

The photograph in FIG. 2 provides a close-up view of the flowers of 'Starlight'.

Figure 3:
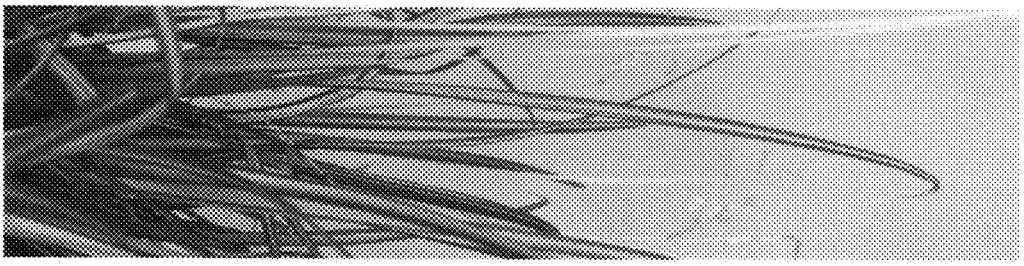

The photograph in FIG. 3 provides a close-up view of the foliage of 'Starlight'.

The colors in the photograph may differ slightly from the color values cited in the detailed botanical description, which accurately describe the colors of the new *Anthericum.*

DETAILED BOTANICAL DESCRIPTION

The following is a detailed description of 2 year-old plants as grown in a greenhouse in 17-cm containers in Boskoop, Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Year around in the Netherlands in a greenhouse.

*Plant type*.—Herbaceous perennial.

*Plant habit*.—Clump-forming, upright and gently cascading.

*Height and spread*.—Average height of 75 cm in height and 50 cm in spread.

*Hardiness*.—At least in U.S.D.A. Zones 8 to 13.

*Plant vigor*.—Moderately vigorous.

*Diseases*.—Not disease problems have been observed, *Anthericum* plants in general are disease free.

*Root description*.—Fleshy, 199D in color, no rhizome were observed.

*Propagation*.—Shoot division.

*Growth rate*.—Vigorous.

*Shoot number*.—Average of 80 shoots in a 17-cm container.

Foliage description:

*Leaf shape*.—Linear.

*Leaf division*.—Simple.

*Leaf base*.—Ranked.

*Leaf apex*.—Long acuminate.

*Leaf venation*.—Parallel, mid rib 145B in color on upper surface and 155D on lower surface, other viens match leaf color.

*Leaf margins*.—Entire.

*Leaf size*.—Matures to an average of 46 cm in length and 6.5 mm in width.

*Leaf number*.—Average of 12 leaves per shoot.

*Leaf arrangement*.—Alternate, ranked, grass-like.

*Leaf surface*.—Both surfaces glabrous, dull and ridged.

*Leaf aspect*.—Emerges upright and gently cascades as they mature, canaliculate with lower mid protruding on lower surface.

*Leaf color*.—Young foliage (on new shoots) upper and lower surface; color between 137D and 144A, mature upper surface; 137B with mid rib and stripes in centers 145A to 145D, mature lower surface; 137B with mid rib and stripes in center 155D and 145D and suffused with 167C at base of leaf.

*Petiole*.—None, sessile to base.

Flower description:

*Inflorescence type*.—Branched raceme at teminus of flower scape (peduncle).

*Inflorescence size*.—Reaches up to 10.6 cm in height and about 8.6 cm in width.

*Flower fragrance*.—None.

*Flower quantity*.—Average of 25 per branched raceme.

*Flower lastingness*.—An average of 1 week, only bract is persistent.

*Flower buds*.—Oval in shape, an average of 3 mm in diameter and 5 mm in length, a blend of 10D, 18D and 17A in color, glabrous surface.

*Flower aspect*.—Held outward from peduncle (rachis).

*Flower shape*.—Rotate.

*Flower size*.—About 1.2 cm (with pistil) in depth and 2 cm in diameter.

*Tepals*.—6 (2 rows of 3), outer sepals; narrow elliptic to oblanceolate in shape, an average of 1 cm in length and 3 mm in width, inner sepals; elliptic in shape, an average of 1 cm in length and 5 mm in width, all tepals; entire margin, acute apex, cuneate base, non overlapping, upper and lower surfaces are glabrous, smooth and shiny, color of upper surfaces (inner side); NN155D, tips are 17B, center rib fades from the bottom to the tip a blend of 17C and 16C, lower surface (outer side);

*Bracts*.—At base of petiole, dry and membranous on both surfaces, typically 3, lanceolate with center one larger with an extensed awn, an average of 3 mm in length and 2 mm in width with awn 4 mm in length and very fine, a blend of 200B and 155C in color.

*Peduncles*.—Main scape; 40 cm in length (to base of racemes) and 3 mm in width at center (narrowing to 1 mm at apex), oval-flat in shape, glabrous surface, 1C in color, raceme rachis; an average of 3, oval-flat in shape, an average of 5.8 cm in length and 1 mm in width, flower internode length an average of 4 mm, glabrous surface, 11C in color.

*Pedicels*.—Round and wider at apex, moderately strong, an averge of 4 mm in length and 0.7 mm in width, held at a 45° angle to peduncle, glabrous surface, 163D in color.

Reproductive organs:

*Gynoecium*.—1 Pistil, stigma is an average of 0.3 mm in length and width, and 155A in color, style is cylindrical, about 8 mm in length and <1 mm in width and NN155D in color, ovary is superior, globose-obovate in shape, about 1.5 mm in length and 1 mm in width and 7A in color.

*Androcoecium*.—6 stamens, anthers are an average of 3 mm in length and 0.8 mm in width and a blend of 7B and 17B in color, filaments are about 1.5 mm in length and NN155C in color, pollen is moderate in quantity and a blend of 7B and 17B in color.

It is claimed:

1. A new and distinct cultivar of *Anthericum* plant named 'Starlight' as herein illustrated and described.

* * * * *